(12) United States Patent
Hernandez

(10) Patent No.: US 10,478,136 B2
(45) Date of Patent: Nov. 19, 2019

(54) RADIOLOGICAL DOSING SYSTEM AND METHOD

(71) Applicant: Certa Dose, Inc., Denver, CO (US)

(72) Inventor: Caleb Hernandez, Arvada, CO (US)

(73) Assignee: Certa Dose, Inc.

( * ) Notice: Subject to any disclaimer, the term of this patent is extended or adjusted under 35 U.S.C. 154(b) by 271 days.

(21) Appl. No.: 15/592,990

(22) Filed: May 11, 2017

(65) Prior Publication Data

US 2017/0245811 A1 Aug. 31, 2017

Related U.S. Application Data

(63) Continuation-in-part of application No. 15/588,497, filed on May 5, 2017, and a continuation-in-part of
(Continued)

(51) Int. Cl.
*A61N 5/10* (2006.01)
*A61B 6/10* (2006.01)
(Continued)

(52) U.S. Cl.
CPC ............... *A61B 6/10* (2013.01); *A61B 6/027* (2013.01); *A61B 6/481* (2013.01); *A61M 5/178* (2013.01);
(Continued)

(58) Field of Classification Search
CPC ........... A61B 6/10; A61B 6/481; A61B 6/027; A61M 5/178; A61M 5/31533; A61M 5/007; A61M 5/14; A61M 5/3129; A61M 5/315; A61M 2005/3126; A61M 2205/584; A61N 5/1007; A61N 2005/1021; A61N 5/1042; A61N 5/1049; A61N 5/1048; A61N 5/1031; G06F 19/3481
See application file for complete search history.

(56) References Cited

U.S. PATENT DOCUMENTS

D280,734 S 9/1985 Bateman
4,713,888 A 12/1987 Broselow
(Continued)

FOREIGN PATENT DOCUMENTS

EP 0983761 3/2000
EP 2548597 A1 1/2013
(Continued)

OTHER PUBLICATIONS

Supplementary European Search Report for European Application No. 13742871.0, dated Jul. 17, 2015, 6 pages.
(Continued)

*Primary Examiner* — Kiho Kim
(74) *Attorney, Agent, or Firm* — Cooley LLP

(57) ABSTRACT

Aspects of the present disclosure disclose a system and method for delivering for administering radiation to a patient. The method may include associating the patient with one of a plurality of coded dosage zones wherein each of the plurality of coded dosage zones corresponds to one or more values of a physical characteristic. The method may further include correlating the one of the plurality of coded dosage zones to a dose of radiation and then applying the dose of radiation to the patient.

15 Claims, 12 Drawing Sheets

Related U.S. Application Data application No. 15/282,732, filed on Sep. 30, 2016, and a continuation-in-part of application No. 14/392,087, filed as application No. PCT/US2013/023873 on Jan. 30, 2013.

(60) Provisional application No. 62/334,990, filed on May 11, 2016, provisional application No. 61/717,474, filed on Oct. 23, 2012, provisional application No. 61/593,674, filed on Feb. 1, 2012.

(51) Int. Cl.
| | |
|---|---|
| *A61B 6/02* | (2006.01) |
| *A61M 5/178* | (2006.01) |
| *A61B 6/00* | (2006.01) |
| *A61M 5/315* | (2006.01) |
| *A61M 5/14* | (2006.01) |
| *A61M 5/00* | (2006.01) |
| *A61M 5/31* | (2006.01) |

(52) U.S. Cl.
CPC ....... *A61M 5/31533* (2013.01); *A61N 5/1007* (2013.01); *A61N 5/1042* (2013.01); *A61N 5/1049* (2013.01); *A61N 5/1071* (2013.01); *A61M 5/007* (2013.01); *A61M 5/14* (2013.01); *A61M 5/315* (2013.01); *A61M 5/3129* (2013.01); *A61M 2005/3126* (2013.01); *A61M 2205/584* (2013.01); *A61N 2005/1021* (2013.01)

(56) References Cited

U.S. PATENT DOCUMENTS

| | | | |
|---|---|---|---|
| 4,716,888 A | 1/1988 | Wesner | |
| 4,823,469 A | 4/1989 | Broselow | |
| 4,926,885 A | 5/1990 | Hinkle | |
| 5,010,656 A | 4/1991 | Broselow | |
| 5,016,651 A | 5/1991 | Stalcup et al. | |
| 5,468,224 A | 11/1995 | Souryal | |
| 5,573,529 A | 11/1996 | Haak et al. | |
| 5,692,640 A | 12/1997 | Caulfield et al. | |
| 5,773,258 A | 6/1998 | Birch et al. | |
| 6,132,416 A | 10/2000 | Broselow | |
| 6,322,543 B1 | 11/2001 | Singh et al. | |
| 6,338,200 B1 | 1/2002 | Baxa et al. | |
| 6,764,469 B2 | 7/2004 | Broselow | |
| D500,342 S | 12/2004 | Stewart et al. | |
| D500,524 S | 1/2005 | Stewart et al. | |
| D547,658 S | 7/2007 | Small et al. | |
| D548,241 S | 8/2007 | Viegers | |
| 7,857,138 B2 | 12/2010 | Temple | |
| 8,062,254 B2 | 11/2011 | MacLean | |
| 8,182,450 B2 | 5/2012 | Moosheimer et al. | |
| 8,361,055 B2 | 1/2013 | Tucker | |
| D684,467 S | 6/2013 | Macaulay et al. | |
| D684,468 S | 6/2013 | Macaulay et al. | |
| D686,492 S | 7/2013 | DiFranza | |
| D687,707 S | 8/2013 | Craig et al. | |
| 8,535,277 B2 | 9/2013 | Oden et al. | |
| 9,019,307 B1 | 4/2015 | Grimm | |
| D741,871 S | 10/2015 | Chung et al. | |
| 9,159,249 B2 | 10/2015 | Ferrara | |
| 9,192,723 B2 | 11/2015 | Creaturo | |
| D745,534 S | 12/2015 | Cho | |
| D747,726 S | 1/2016 | Virk et al. | |
| D748,105 S | 1/2016 | Virk et al. | |
| 9,271,896 B2 | 3/2016 | Clements | |
| 9,272,099 B2 | 3/2016 | Limaye et al. | |
| 9,345,638 B2 | 5/2016 | Ferrara | |
| 9,345,639 B2 | 5/2016 | Ferrara | |
| D771,807 S | 11/2016 | Zalewski | |
| D783,397 S | 4/2017 | Riffe | |
| 9,682,195 B2 | 6/2017 | Tucker | |
| D797,759 S | 9/2017 | Tsujimura et al. | |
| D798,886 S | 10/2017 | Prophete et al. | |
| 9,839,750 B2 | 12/2017 | Limaye et al. | |
| 9,931,469 B2 | 4/2018 | Shain et al. | |
| 9,950,126 B2 | 4/2018 | Basile et al. | |
| D819,060 S | 5/2018 | Friedman et al. | |
| D846,383 S | 4/2019 | Hernandez | |
| 2002/0087121 A1 | 7/2002 | Slishman | |
| 2002/0088131 A1 | 7/2002 | Baxa et al. | |
| 2004/0024368 A1 | 2/2004 | Broselow | |
| 2004/0082855 A1* | 4/2004 | Robar | A61N 5/10 600/436 |
| 2004/0186437 A1 | 9/2004 | Frenette et al. | |
| 2005/0090782 A1 | 4/2005 | Marshall et al. | |
| 2005/0215957 A1 | 9/2005 | Hynes | |
| 2006/0000480 A1 | 1/2006 | Broselow | |
| 2006/0137696 A1 | 6/2006 | Broselow | |
| 2007/0100288 A1 | 5/2007 | Bozeman et al. | |
| 2007/0127623 A1* | 6/2007 | Goldman | A61N 5/1031 378/65 |
| 2007/0135772 A1 | 6/2007 | Grogan, Jr. | |
| 2007/0201614 A1* | 8/2007 | Goldman | A61N 5/1031 378/65 |
| 2008/0188814 A1 | 8/2008 | Lavi-Loebl et al. | |
| 2008/0232542 A1 | 9/2008 | Lin | |
| 2009/0126743 A1 | 5/2009 | Wingert | |
| 2009/0149815 A1 | 6/2009 | Kiel et al. | |
| 2010/0056895 A1 | 3/2010 | Temple et al. | |
| 2013/0012886 A1 | 1/2013 | Kawachi | |
| 2013/0101079 A1 | 4/2013 | Hough et al. | |
| 2013/0204225 A1 | 8/2013 | Creaturo | |
| 2015/0057608 A1 | 2/2015 | Hitscherich, Jr. et al. | |
| 2015/0306318 A1 | 10/2015 | Lockhart et al. | |
| 2016/0022912 A1 | 1/2016 | Hernandez | |
| 2016/0022920 A1 | 1/2016 | Reeves | |
| 2016/0136050 A1 | 5/2016 | Clements | |
| 2016/0166774 A1 | 6/2016 | Leary | |
| 2016/0166775 A1 | 6/2016 | Oakley et al. | |
| 2016/0250416 A1 | 9/2016 | Hultgren | |
| 2017/0095615 A1 | 4/2017 | Fischer et al. | |
| 2017/0151391 A1 | 6/2017 | Hernandez | |
| 2017/0304152 A1 | 10/2017 | Hernandez | |
| 2017/0367930 A1 | 12/2017 | Gompf et al. | |
| 2018/0043103 A1 | 2/2018 | Nandigala et al. | |
| 2018/0154088 A1 | 6/2018 | Broselow | |
| 2018/0221581 A1 | 8/2018 | Kumar et al. | |

FOREIGN PATENT DOCUMENTS

| | | |
|---|---|---|
| GB | 2461013 A | 12/2009 |
| JP | 2008-171582 A | 7/2008 |
| JP | 2011-143652 A | 7/2011 |
| WO | WO 2010/112558 | 10/2010 |
| WO | WO 2011/114917 | 9/2011 |
| WO | WO 2013/116353 | 8/2013 |
| WO | WO 2017/193082 | 11/2017 |
| WO | WO 2017/197145 | 11/2017 |

OTHER PUBLICATIONS

International Search Report and Written Opinion for International Application No. PCT/US2013/023873, dated Jun. 2, 2013, 12 pages.
International Search Report and Written Opinion for International Application No. PCT/US2017/031420, dated Aug. 14, 2017, 6 pages.
International Search Report and Written Opinion for International Application No. PCT/US2017/032207, dated Jul. 26, 2017, 9 pages.
Critical Care Medicine; "A pediatric gastric tube airway," The Williams & Watkins Co.; 9(5):426-427 (1981).
"Color Coding System Measures Kids' Meds," Healthy Living, KABC-TV/DT, Mar. 24, 2009, 5 pages.
McFadden, M., "New dosing system takes the guesswork out of giving medicine to kids," WNDU—Channel 16, Mar. 12, 2009, 3 pages.
Moreira, M. E. et al., "Color-Coded Prefilled Medication Syringe Decrease Time to Delivery and Dosing Error in Simulated Emer-

(56) References Cited

OTHER PUBLICATIONS gency Department Pediatric Resuscitations," Annals of Emergency Medicine, United States of America, American College of Emergency Physicians, Aug. 2015, vol. 66, No. 2, pp. 97-106.

HMC Pharmacy, "New Procedure: Emergency syringes," Harborview Medical Center (Oct. 2010), 1 page.

Frush, K. S. et al., "Evaluation of a Method to Reduce Over-the-Counter Medication Dosing Error," Arch. Pediatr. Adolesc. Med., 158:620-624 (Jul. 2004).

International Search Report and Written Opinion for International Application No. PCT/US2019/014623, dated Apr. 12, 2019, 12 pages.

Med Alliance Group, Inc., Certa Dose Epinephrine Convenience Kit, Accurate Dosing Confirmed [Online], Retrieved from the Internet on Jun. 20, 2018; <URL: https://www.medalliancegroup.com/product/certadose-epinephrine/>, 3 pages.

Excel Spreadsheets Group, 4+ Simple Excel Spreadsheet [Online], Retrieved from the Internet on Feb. 20, 2018; <URL:http://excelspreadsheetsgroup.com/4-simple-excel-spreadsheet/>, 4 pages.

Ryu, G. S. et al. "Analysis of liquid medication dose errors made by patients and caregivers using alternative measuring devices", J Manag Care Pharm. Jul.-Aug. 2012;18(6):439-45.

Luten, R. et al. "Managing the unique size-related issues of pediatric resuscitation: reducing cognitive load with resuscitation aids", Acad Emerg Med. Aug. 2002;9(8):840-7.

Moreira, M. E., et al. "Novel, Color-Coded Prefilled Syringe Significantly Decreases Time to Medication Administration, Preparation for Endotracheal Intubation, and Eliminates Critical Dosing Errors in Simulated Pediatric Resuscitations," Circulation. Journal of the American Heart Association. Dec. 4, 2012. 126(23): 2798. LBRS-358.

Melker, R. et al. "A pediatric gastric tube airway," Critical Care Medicine. 1981. The Williams & Watkins Co.; 9(5):426-427.

* cited by examiner

RADIOLOGICAL DOSING SYSTEM AND METHOD

CROSS REFERENCE TO RELATED APPLICATIONS

This application claims priority to and the benefit of U.S. Provisional Patent Application No. 62/334,990, filed May 11, 2016, entitled "Radiological Dosing System and Method." This application is also a continuation-in-part of U.S. patent application Ser. No. 15/588,497, filed May 5, 2017, entitled "Apparatuses, Methods, and Systems for Delivering Medication Using Medication Kits," and a continuation-in-part of U.S. patent application Ser. No. 15/282,732, filed Sep. 30, 2016, entitled "Apparatuses, Methods, and Systems for Delivering Measured Doses of Medication," and a continuation-in-part of U.S. patent application Ser. No. 14/392,087, filed Sep. 2, 2015, entitled "System for Delivering Medication," which is a national stage entry of PCT Application No. PCT/US2013/023873, filed Jan. 30, 2013, entitled "System for Delivering Medication," which claims priority to U.S. Provisional Application No. 61/593,674, filed Feb. 1, 2012, entitled "System for Delivering Medication," and to U.S. Provisional Application No. 61/717,474, filed Oct. 23, 2012, entitled "System for Delivering Medication." All of the above-referenced applications are hereby expressly incorporated by reference herein.

FIELD OF DISCLOSURE

The present disclosure relates to methods for determining and administering appropriate doses of radiation.

BACKGROUND

Administering proper drug doses accurately and efficiently is of critical importance. This is essential when determining and/or delivering a dose of radiation to a pediatric patient, since even small dosing mistakes can lead to disastrous consequences. Further, radiation treatments carry additional risks when an overdose is delivered, such as radiation overdose, radiation poisoning, and even development of cancer. Some patients receiving radiation treatments may also receive IV contrast media and/or sedation. (As referred to herein, the term "contrast media" may also refer to contrast dye or contrast agent.) This carries additional steps where errors may be made, and an overdose of IV contrast media could lead to permanent kidney damage and/or kidney failure.

Even under the best of circumstances and despite the best of efforts of medical personnel, inadvertent mistakes are sometimes made because of the multitude of steps involved in administering radiation. More specifically, in a typical situation appropriate dosage must first be determined, which usually involves multistep mathematical calculations. This is followed by plurality of steps involved in the actual administration process, which may include selection of a correct dosage to be administered, including the intensity and the time period of the dose applied. Moreover, a number of other calculations, such as those involving, for example, intensity of the radiation and the time period for application, are required to be performed as part of the process of administration.

Problems in dosage accuracy may be further compounded by emergencies, inexperienced staff, distractions, and/or dosing radiation and intravenous contrast media and/or sedation simultaneously or in quick succession.

SUMMARY

In one aspect, the disclosure relates to method of administering radiation to a patient. The method may include associating the patient with one of a plurality of coded dosage zones wherein each of the plurality of coded dosage zones corresponds to one or more values of a physical characteristic. The method may further include correlating the one of the plurality of coded dosage zones to a dose of radiation and applying the dose of radiation to the patient. The dose of radiation may depend on a location on the patient where the radiation is to be applied. In some embodiments, the physical characteristic may be at least one of: weight, length, and surface area.

The disclosure also pertains to a method of administering radiation to a patient. The method includes receiving, at a processor associated with a radiation device, information indicating that a patient is associated with a coded region included among a plurality of coded regions wherein each of the plurality of coded regions corresponds to one or more values of a physical characteristic. The method further includes receiving, at the processor, a radiation location for the patient. The processor may correlate the coded region and the radiation location with a dose of radiation. The method further includes applying the dose of radiation to the patient at the radiation location.

In some embodiments, the processor may determine a patient size. Additionally, a safe range of radiation for the patient may be determined at the processor and based on patient size. The application of the dose of radiation to the patient may include verifying that the dose of radiation to be given to the patient is within the safe range.

In some implementations, the patient size may be correlated to one of the plurality of coded regions. The coded regions may be color coded. In some embodiments, the safe range of radiation is determined based on the radiation location.

In other implementations, the method may further include receiving, at the processor, additional information indicating that an additional patient is associated with an additional coded region included among the plurality of coded regions. An additional radiation location for the additional patient may also be received at the processor. The additional coded region and the additional radiation location may be correlated, at the processor, with an additional dose of radiation. A safe range of radiation for the additional patient may be calculated at the processor and based on patient size. If it is determined that the additional dose of radiation is not within the safe range, the additional dose of radiation is not applied to the additional patient. In some such embodiments, when the additional dose of radiation is determined not to be within the safe range, a notification may be generated, at the processor, to display on a screen associated with the radiation device.

In another aspect, the disclosure relates to a method for administering radiation to a patient. The method includes receiving, at a processor associated with a radiation device, a calculated dose of radiation for a patient, receiving a radiation location for the patient, and receiving at least one of a patient characteristic and a coded region corresponding to a patient characteristic. The method further includes correlating the patient characteristic and/or coded region corresponding to the patient characteristic with a safe dose range of radiation at the radiation location for the patient.

The processor may compare the calculated dose of radiation to the safe dose range. The calculated dose of radiation is applied to the patient at the radiation location when the calculated dose of radiation is within the safe dose range. In some embodiments, when the calculated dose of radiation is not within the safe dose range, a message may be generated and displayed on a screen associated with the radiation device, and the calculated dose of radiation is not applied to the patient at the radiation location.

In some embodiments, the safe dose range for the patient may vary depending on the radiation location.

In some implementations, the method may further include determining a second patient characteristic at the radiation location. A second coded region may be determined at the processor and based on the second patient characteristic. The second coded region for the patient may be correlated, at the processor, with a second safe dose range of radiation at the radiation location for the patient. The processor may determine that the calculated dose is within the second safe dose range. The calculated dose may be applied when the calculated dose is within the safe dose range and the second safe dose range. When the calculated dose is not within the safe dose range and within the second safe dose range, a message to display may be generated, and the message may be displayed on a screen associated with the radiation device.

In some embodiments, the method may further include determining a second patient characteristic at the radiation location. A second coded region for the patient may be determined at the processor and based on the second patient characteristic. A message to display may be generated when the second coded region is not the same as the coded region, and the message may be displayed on a screen associated with the radiation device.

In another aspect the disclosure is directed to a method of administering radiation to a patient. The method includes receiving, at a processor associated with a radiation device, information identifying a color coded region corresponding to a value of a physical characteristic of the patient wherein the color coded region is included among a plurality of color coded regions. The method further includes receiving, at the processor, a radiation location corresponding to a location on a patient. The processor may then determine that at least one of contrast media and sedation are to be given to the patient and may further determine, based at least in part on the color coded region, at least one of a dose amount and a dose concentration of the at least one of the contrast media and sedation. The method may further include correlating the color coded region and the radiation location with a dose of radiation and providing the at least one of the contrast media and sedation to the patient. The dose of radiation may then be applied to the radiation location.

DETAILED DESCRIPTION

Figure 1:
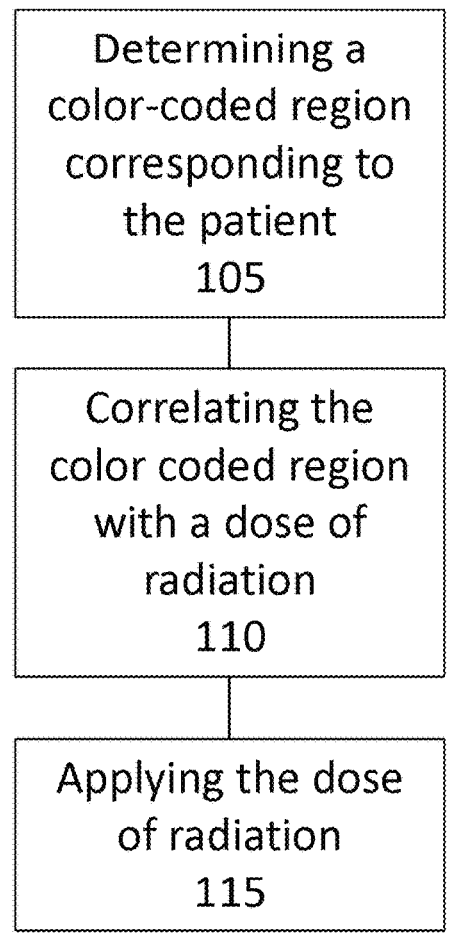
FIG. 1 is a flow diagram showing a method of administering a radiation dose according to an embodiment.

The present application describes a device, system, and method for administering proper radiation and/or medication doses to patients. A dose of radiation may be determined by an intensity and a time period over which the radiation is applied to the patient. In determining the dose for a particular patient, the size of the patient, the location on the body where the radiation is applied, and the radiation type (i.e., CT scan, X-ray, etc.) may be taken into account. Additionally, some types of radiation are applied in conjunction with IV contrast media and/or sedation. Doses of IV contrast media and doses of sedation, including whether or not contrast media and/or sedation are necessary, are also dependent on the size of the patient, the type of radiation being applied, and the location of the radiation.

At least in part because of all of the factors that must be considered for dosing radiation, IV contrast media, and sedation, errors can occur in determining the dose for one or all of these. These errors can have significant implications for patients, including radiation overdose, radiation poisoning, development of cancer, kidney damage, kidney failure, and the like. Thus, simplifying and removing the need for complicated calculations can significantly reduce the risk incurred by patients receiving such treatments.

To achieve this, dosages can be standardized into various zones that are determined based on patient size. Patient size can be determined based on patient weight, length, surface area, and/or other factors. Once the patient size is determined, the size can be correlated to a zone. For example, zones may comprise ranges based on patient weight and/or patient length, so when a patient is measured, the measurement may be within one of the zones.

In one embodiment, a color coded measuring tape may be used to determine a zone with which the length of a patient is correlated. For example, the Broselow® Pediatric Emergency Tape is a well known instrument that correlates easily obtainable patient length to drug dosages. The details of the instrument and the method of its use are disclosed in, for example, U.S. Pat. Nos. 4,716,888 and 6,132,416, which are incorporated by reference into the present disclosure. In general, the method involves measuring and coding patient length to one of the color zones provided on the tape and using the color-coded length to determine a drug dosage to be administered to the patient. By segmenting the tape into plurality of color coded zones rather than the typically used inches or centimeters, with each color zone corresponding to a given length range, the length of the patient can be easily read and noted as being of a certain color rather than as a specific measurement in centimeters or inches. In other words, each color-coded length zone corresponds to a certain, predetermined range of the actual lengths as measured in either metric or imperial units. For example, the grey color zone on the tape may correspond to a length range from 42.20 cm to 60.79 cm and the pink color zone on the tape may correspond to the length range from 60.80 cm to 67.79 cm. Thus, a patient whose length falls within the first length range would be coded as gray and a patient whose length falls within the second length range would be coded as pink. The appropriate drug dosages for the two patients would then be selected from a list of predetermined drug dosages listed on the tape.

In one embodiment, each patient zone may each be assigned a particular symbol, number, and/or the like in lieu of being assigned to a particular color. In the embodiment in which zones are associated with colors, the color coding used may be the same as, or correlated to, the colors used on the Broselow® tape. In such embodiments, a patient that measures into a particular color zone using the Broselow® tape will receive the dose of radiation, IV contrast media, and/or sedation that correlates to that color zone. In some embodiments, there may be nine (9) standardized zones, which may each be associated with one of nine colors.

Additionally, the dose of radiation for a patient depends on where on the body the radiation is being applied. For example, the intensity and/or time period for a dose of radiation to the head is different than the intensity and/or time period for a dose of radiation to the abdomen, even within the same patient or for patients of similar size. Thus, the standardizations for radiation would include dosages depending on where the radiation is applied. So, for example, once a patient is assigned to the "yellow" zone, the amount of radiation given is dependent on the area of application, so the "yellow" zone includes a radiation dose for a head CT, a chest CT, and/or the like. The zone may also include doses for different types and concentrations of IV contrast media and sedation.

As a result, instead of having multiple calculations, the technician, nurse, physician, and/or the like only needs to know the color range that correlates to the patient size (weight, length, etc.). The color range determines at least the intensity of radiation and the time frame for the application of the radiation for each location on the body (e.g., head, arm, leg, abdomen, chest, etc.).

In order to determine the dose, a technician, nurse, and/or physician may read a chart/table. For example, the colors may be listed across the top, and the locations of radiation may be listed down the side, and the intensity and time frames for each color and location may be listed within each box. In another embodiment, the determination may be a part of the radiation delivery machine, such as the X-Ray or CT machine. The technician may determine the color zone based on the patient size and may enter the color into the machine. The machine may then perform, based upon the patient's color zone, known dosing calculations and deliver a dose of radiation to the patient appropriate for the associated color zone. In some embodiments, the technician may enter the patient size based on weight and/or length, and the machine may determine the color and/or appropriate dose and deliver the dose to the patient color zone.

In yet another embodiment, the technician, nurse, physician, and/or the like may perform the calculations to determine the dose for a patient. The determined dose may then be verified against the color range that correlates to the patient size. This way, if an error is made in the calculation, the technician, nurse, physician, and/or the like will be able to quickly verify that the determined dose is within the color range determined for that patient. This way, the calculations are performed, and then verified to be within the proper zone for that patient.

FIG. 1 shows an exemplary flow chart according to one embodiment. A color-coded region may be determined based on the size of the patient (stage 105). As discussed above, the size of the patient may be based on the patient's weight, length, surface area, and/or the like. The size may be within one of a plurality of zones, where each zone corresponds to a particular color, number, symbol, and/or the like. For example, the colors may be similar to or the same as the colors on the Broselow tape. Once the color coded region is determined, the color coded region may be correlated to a dose of radiation (stage 110), and the dose of radiation may be applied (stage 115).

Figure 2A:
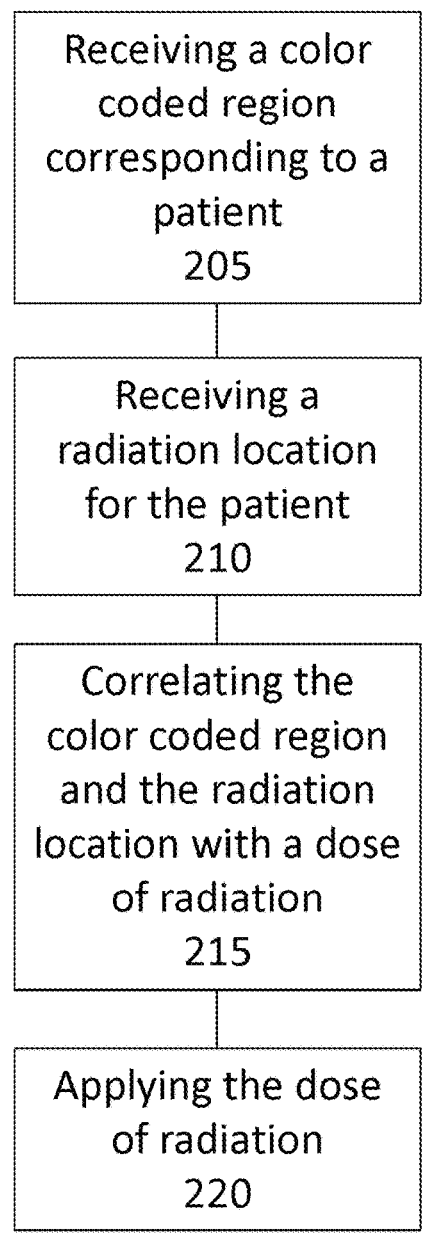
FIGS. 2A-2B are flow diagrams showing method of administering a radiation dose according to other embodiments.

FIG. 2 shows another exemplary flow chart according to an embodiment in which a radiation device, such as an X-Ray machine, CT machine, and/or the like, may determine a dose of radiation in accordance with the methods disclosed herein. Referring to FIG. 2A, a color coded region corresponding to a patient may be received (stage 205). In some embodiments, the color coded region may be entered by a technician, nurse, and/or physician. In other embodiments, the machine may determine the size of the patient, for example, using a built-in scale to determine the weight of the patient, and the machine may be able to determine, based on the size of the patient, a color coded region that corresponds to the patient size. A radiation location may also be received (stage 210). Again, the radiation location may be entered by the technician, nurse, and/or physician, or the machine may be able to determine the location. The color coded region and the radiation location may be correlated with a dose of radiation (stage 215). The dose of radiation may include an intensity and time frame that the intensity of radiation should be applied. The dose of radiation may be applied (stage 220).

Figure 2B:
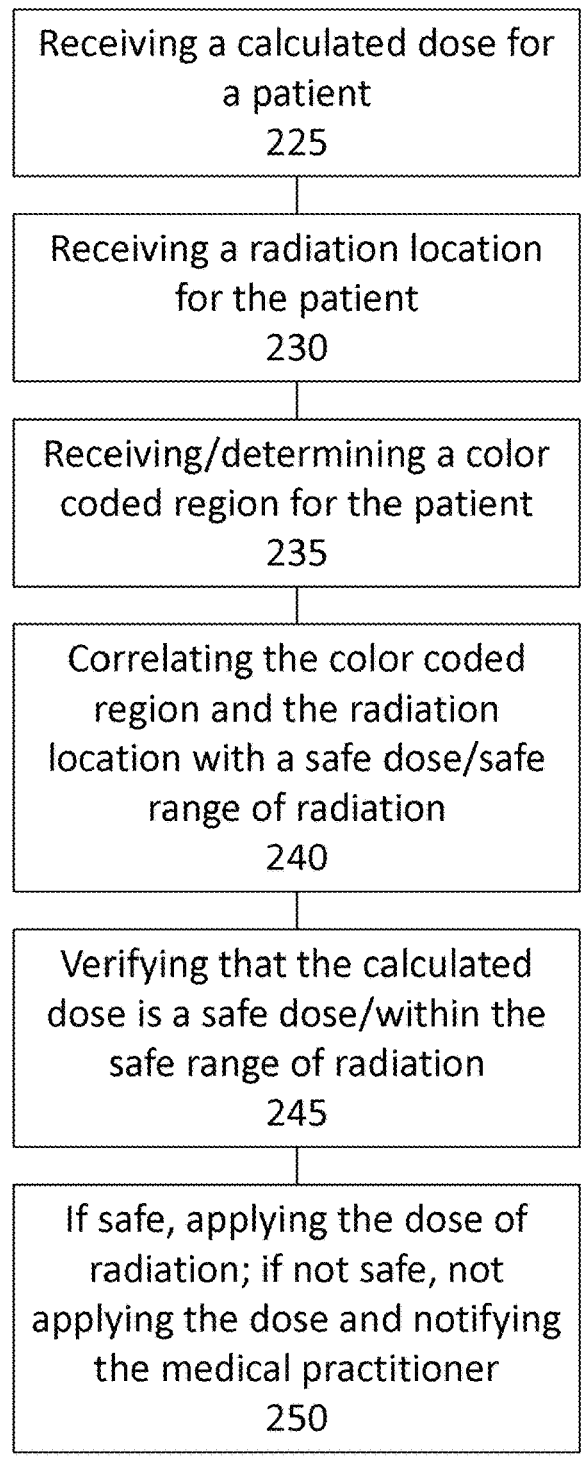

In another embodiment, as shown in FIG. 2B, the technician, nurse, physician, and/or the like may calculate a dose for a patient and enter the calculated dose of radiation and the region to which it may be applied (stage 225, 230). The color coded region corresponding to the patient may be entered by the technician, nurse, physician, and/or the like, and/or the machine may determine the size of the patient, as discussed above, and may correlate the patient size to a color coded region (stage 235). The machine may correlate the color coded region and radiation location may be correlated with a safe dose of radiation and/or a safe range of doses of radiation (stage 240). The machine may verify that the dose entered by the technician, nurse, physician, and/or the like is a safe dose and/or within the safe range (stage 245). Once the machine determines that the dose is safe, the machine may apply the dose to the region. If the dose is not safe, the machine may not apply the dose. The machine may also provide a notification to the technician, nurse, physician, and/or the like that the dose is not safe for the patient (stage 250).

Figure 3:
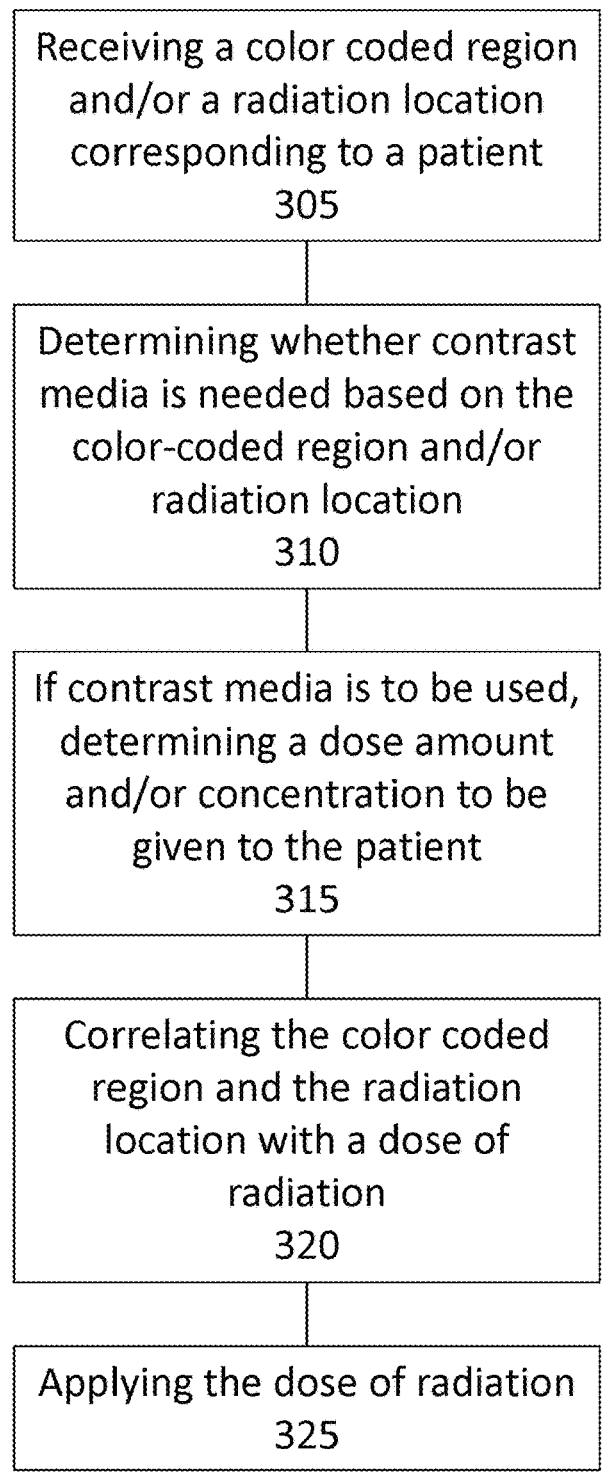
FIG. 3 is a flow diagram showing a method of administering a radiation dose according to another embodiment.

As shown in FIG. 3, in some embodiments, a color coded region and/or a radiation location corresponding to a patient may be received 305. As discussed with respect to FIGS. 2A-B, the region and/or location may be entered or determined, depending on the embodiment. Based on the color coded region and/or the radiation location, a determination may be made as to whether contrast media is needed (stage 310). If contrast media is to be used, a dose amount and/or concentration to be given to the patient may be determined (stage 315). In some embodiments, the dose and/or concentration may be displayed to a technician, nurse, and/or physician. A similar determination may be made with respect to sedation, such that a determination as to whether sedation is required may be made and a dose and/or concentration may be displayed to a technician, nurse, and/or physician. The dose and/or concentration of the contrast media and/or sedation to be applied may depend on the size of the patient, the color coded region, and/or the radiation location. Additionally, the color coded region and the radiation location are also correlated with a dose of radiation to be applied to the patient (stage 320), and the dose of radiation is applied (stage 325). The application of the dose may be delayed in order to ensure that the contrast media and/or sedation have been given to the patient prior to application of the radiation.

When sedation and/or IV contrast media are applied, a syringe may be marked with predetermined color-coded volumetric doses for the type and/or concentration of the contrast media and/or sedation. This is further described in U.S. application Ser. Nos. 15/588,497, 15/282,732, and 14/392,087 and PCT Application No. PCT/US2013/023873, all of which are hereby expressly incorporated by reference in their entireties.

Figure 4A:
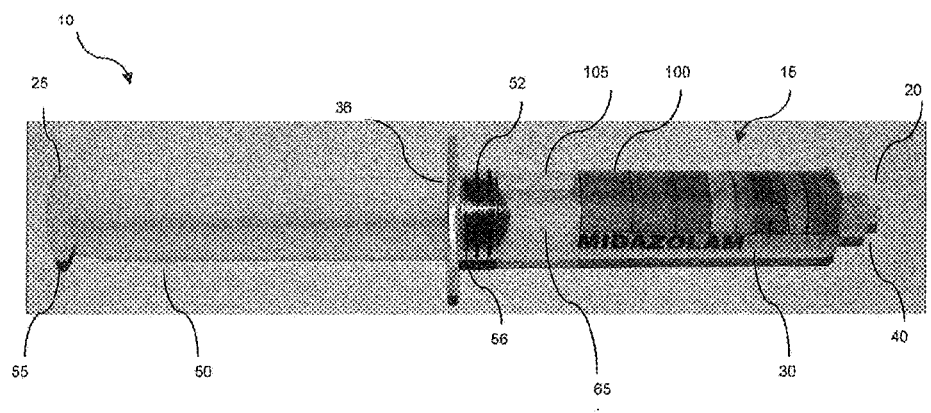
FIGS. 4A-4D show perspective views of an exemplary medicine-dosing device according to some embodiments.

Attention is now directed to FIGS. 4A-4D, which illustrate one embodiment of a medicine dosing device 10 for delivering the IV contrast media and/or sedation. As shown, the dosing device 10 includes a syringe 15 that includes an elongate barrel 30 marked with predetermined color-coded volumetric medicine doses 100 and a plunger 50. The medicine-dosing device, according to one embodiment, may be further pre-filled with a fluid 105 that corresponds to a medication to be administered to a patient. As shown in FIG. 4A, the syringe 15 includes a proximal end 25 and a distal end 20 opposite the proximal end. The syringe 15 further includes a vessel, such as a syringe barrel 30 at the distal end for holding therein a medicine that is to be dispensed, and a plunger 50 that extends proximally from an opening 36 located at the proximal end 35 of the syringe barrel to the proximal end 55 of the plunger at the proximal end 25. The syringe barrel 30 and plunger 50 are both typically manufactured from material such as plastic, glass or any other suitable transparent medical grade material that is inert or will not disrupt the chemical balance of the fluid inside.

Figure 4B:
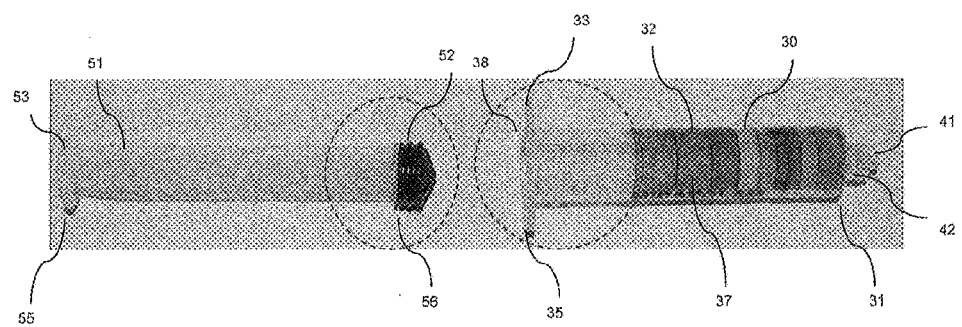
Figure 4C:
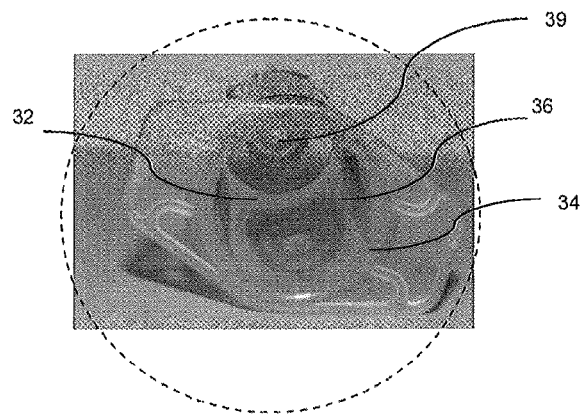
Figure 4D:
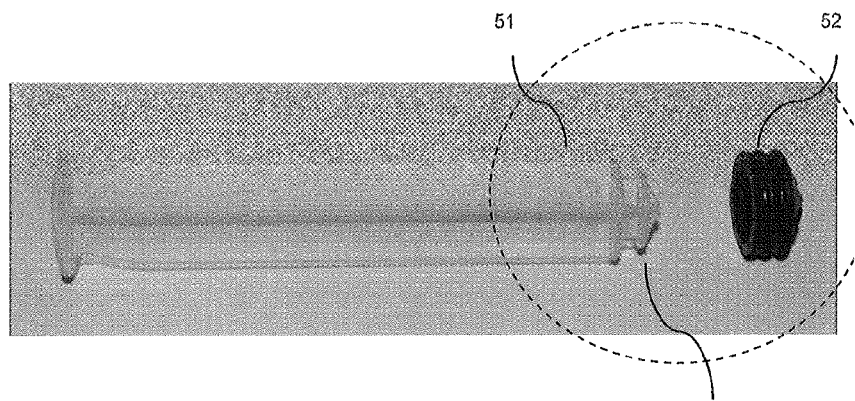

As illustrated in FIG. 4B the syringe barrel 30 is elongate and substantially cylindrical and includes a distal end 31 and a proximal end 35. The syringe barrel further includes and outer circumferential surface 37 and an inner circumferential surface 38. A chamber 32 capable of receiving a plunger and retaining a fluid therein is defined by the inner circumferential surface 38 of the barrel between the distal and proximal ends 31 and 35. A flange 33, which can serve as a finger grip to provide for an easier handing of the syringe, is integrally formed with the proximal end of the barrel and defines an opening 36 for receiving the plunger. Proximate the opening 36, along the inner surface of the barrel, is a ridge 34, shown in FIG. 4C, that prevents the plunger from slipping out of the barrel once it is engaged with the barrel.

The opening 36 is in communication with the chamber 32 and an orifice 39 located at the distal end 20 of the syringe barrel. A tip 40 for attaching a needle, nozzle or tubing for expelling the liquid contained within the syringe barrel 30 is integrally formed with the distal end 20 of the barrel and in communication with the orifice 39. The tip may include coaxially positioned inner 41 and outer 42 members. According to one embodiment the tip may include a Luer taper fitting.

The plunger 50, according to one embodiment shown in FIG. 4B, includes a plunger rod 51 and a rubber or plastic gasket or stopper 52 attached to the distal end 56 of the plunger rod. The gasket forms a tight seal between the inner surface of the barrel and the plunger in order to prevent the contents of the syringe from escaping out the back of the syringe. An annular flange 53 is integrally formed with the proximal end 55 of the plunger rod. The plunger 50 has an elongate shape complementary to that of the chamber 30 and is designed such that it can be pushed along the chamber (inside of the cylindrical barrel or tube) allowing the syringe to expel fluid through the tip 40 or orifice 39 at the distal end of the barrel. Alternatively the plunger can include any other configuration capable of forcing the fluid from inside the chamber 30 through the tip 40 or orifice 39.

According to one embodiment of the present disclosure, the medicine dosing device may be prefilled with a pre-selected drug. Initially, when the medicine dosing device is prefilled and the syringe is in the pre-medication administration position, the substantial length of the plunger rod extends longitudinally outside of the syringe barrel. In other words, as shown in FIG. 4A, prior to the administration of the medicine, only the gasket 52 and the distal end 56 of the plunger rod are initially inside the syringe barrel, at the proximal end 35 of the barrel, with the remaining part of the plunger length outside of the barrel such that its proximal end 55 is in its most extended configuration. Alternatively, in an instance when the medicine dosing device comes as a part of a kit that requires for the drug provided in an included medicine vessel to be drawn into the medicine dosing device immediately prior to the drug administration process, the plunger rod may remain inside the syringe barrel until the drug is drawn into the syringe.

Figure 5A:
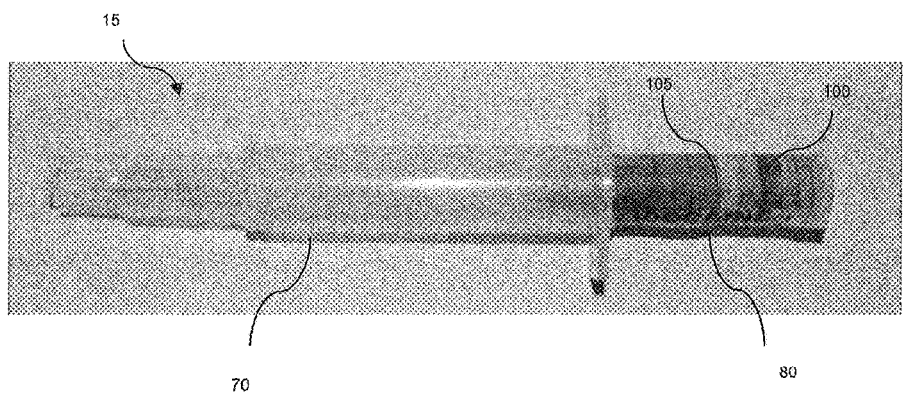
FIGS. 5A-5D show perspective views of an exemplary medicine-dosing device according to other embodiments.
Figure 5B:
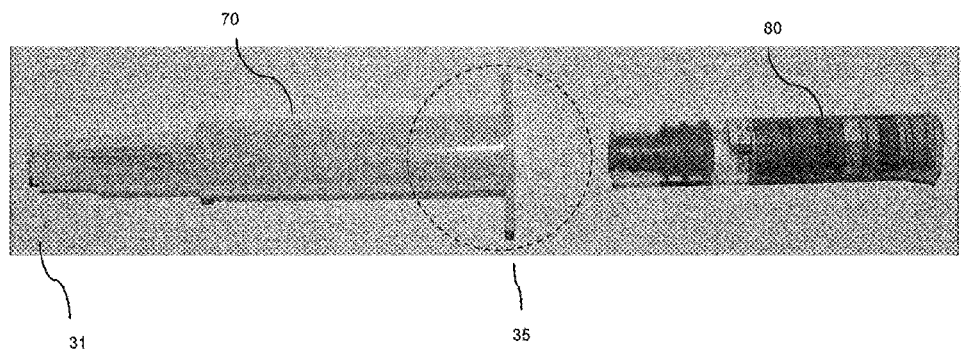
Figure 5C:
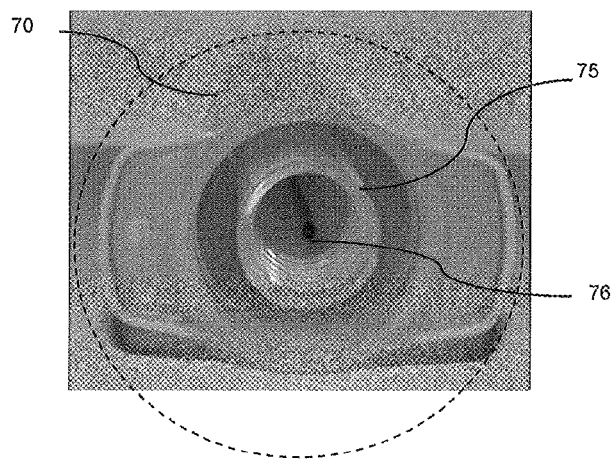
Figure 5D:
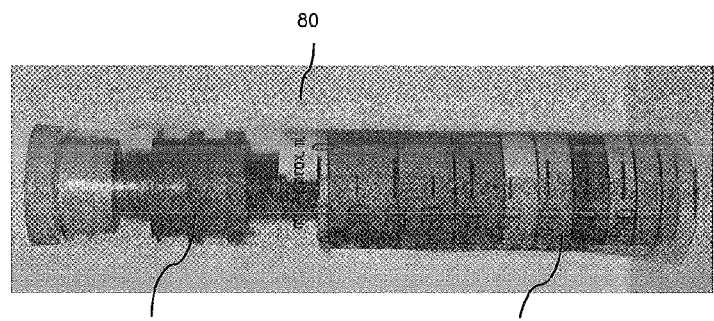

According to another embodiment shown in FIG. 5A, syringe 15 may include an elongate barrel 70 and a plunger 80 marked with predetermined color-coded volumetric medicine doses 100 and prefilled with a fluid 105 that corresponds to a medication to be administered to a patient. In this configuration, as illustrated in FIG. 5C the syringe barrel includes an inner tubular body 75 that is generally coaxially aligned with the larger diameter of the cylindrical barrel. The inner tubular body has a needle 76 coaxially positioned within the inner tubular body and longitudinally aligned with the inner tubular body. The plunger 80, shown in FIG. 5D, includes a substantially cylindrical member or vial 81 and a stopper 82. Because the syringe barrel and the plunger are initially separated, as shown in FIG. 5B, prior to the administration of the medication, the plunger 80 needs to be inserted into the proximal end 35 of the syringe barrel, such that the stopper 82 fully engages with the inner tubular body 75 and the needle 76.

According to yet another embodiment of the current disclosure the plunger and/or plunger stopper can be color coded based on the medication contained in the barrel. Such color coding of the plunger can further increase efficiency with which medication is administered and can make the administration even less error prone as visual inspection of the plunger can provide a quick verification of the correctness of the medication to be administered.

Alternatively the medicine dosing device can include any vessel, such as for example tube, vial, bag or bottle, capable of containing therein and expelling therefrom a desired medicine. For example, the medicine dosing device could be a bag containing an IV fluid. According to this embodiment, the bag may be marked with a series of color coded zones along with the traditional volume markings. When used in combination with the traditional volume markings, the color coded zones could serve as a reminder to the medical personnel of a correct volume of each medication that can be given to a patient based on the patient's color zone. The color coded zones may also be used as a key for entering a correct total volume to be dispensed into the IV pump for a given medication.

The description will now turn to the markings on the surface of the medicine dosing device. In case of a syringe, the markings may be placed along a circumferential surface of the syringe barrel or plunger. As shown in FIGS. 4A through 5D, the markings include a series of substantially translucent bands or zones 100 indicative of the possible medicine doses to be administered to a patient. Although the markings shown in the figures include a series of color coded zones, the markings could also include zones with different patterns, textures, etc. Regardless of the type of the marking used, the markings are either directly imprinted, painted, etched or stained on an inside or outside surface of the medicine dosing device or a label or sleeve may be generated that can be affixed or placed over the outer surface of the medicine dosing device. The applied markings are such that the fluid level, once the device is filled, can be easily seen through the markings.

Figure 6A:
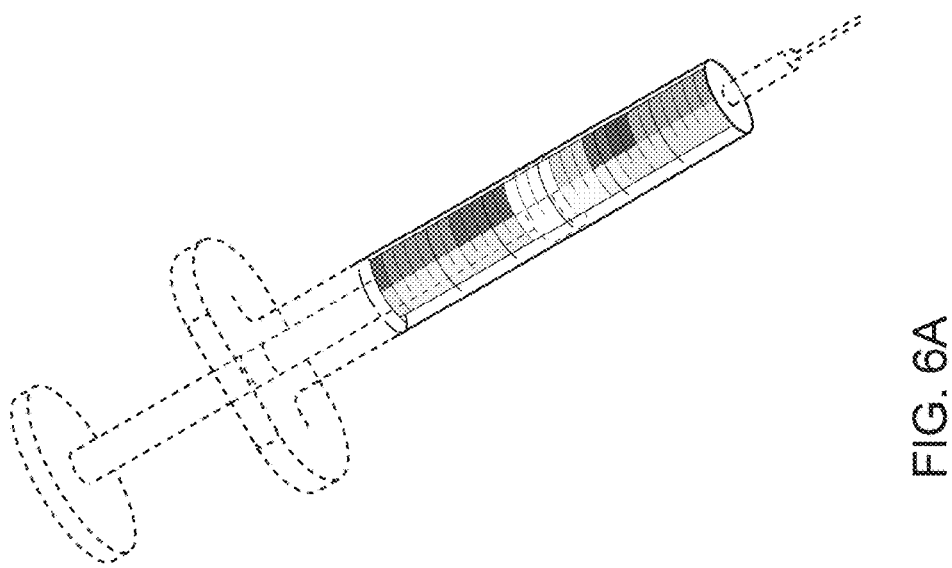
FIGS. 6A-6C show perspective views of an exemplary medicine-dosing device according to other embodiments.
Figure 6B:
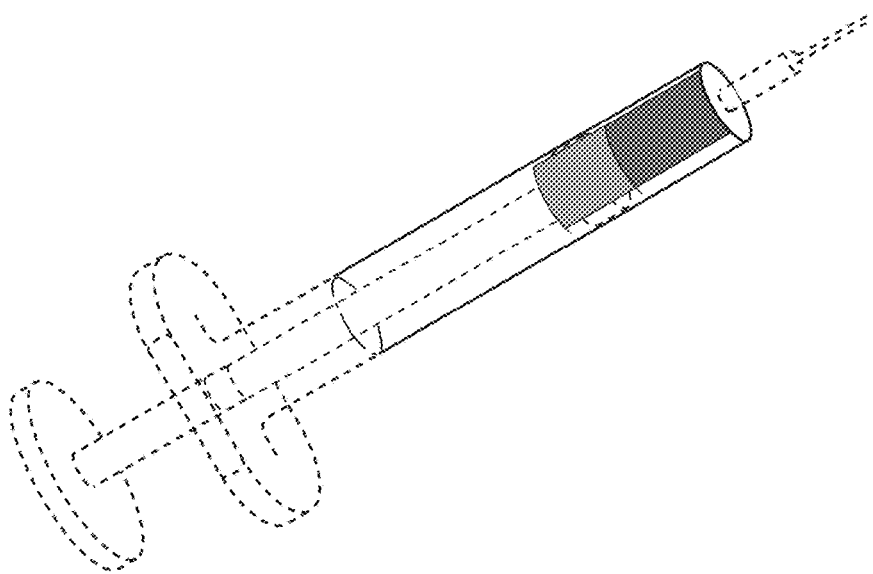
Figure 6C:
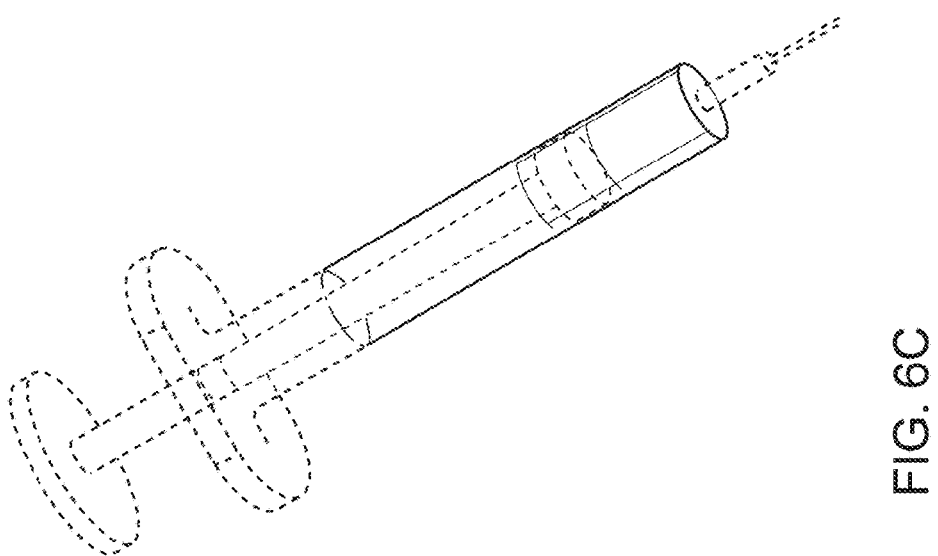

Additional embodiments of medication dosing syringes are shown in FIGS. 6A-6C.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A method of administering radiation to a patient, the method comprising:
   receiving, at a processor associated with a radiation device, information indicating that a patient is associated with a coded region included among a plurality of coded regions wherein each of the plurality of coded regions corresponds to one or more values of a physical characteristic wherein the processor determines a patient size;
   receiving, at the processor, a radiation location for the patient;
   determining, at the processor and based on the patient size, a safe range of radiation for the patient;
   correlating, at the processor, the coded region and the radiation location with a dose of radiation; and
   applying the dose of radiation to the patient at the radiation location.

2. The method of claim 1, wherein the applying includes verifying that the dose of radiation to be given to the patient is within the safe range.

3. The method of claim 1, further including:
   receiving, at the processor, additional information indicating that an additional patient is associated with an additional coded region included among the plurality of coded regions;
   receiving, at the processor, an additional radiation location for the additional patient;
   correlating, at the processor, the additional coded region and the additional radiation location with an additional dose of radiation;
   calculating, at the processor and based on a patient size, a safe range of radiation for the additional patient; and
   determining the additional dose of radiation is not within the safe range and refraining from applying the additional dose of radiation to the additional patient.

4. The method of claim 3, further comprising generating, at the processor, a notification to display on a screen associated with the radiation device upon the determining the additional dose of radiation is not within the safe range.

5. The method of claim 1, wherein the patient size is correlated to one of the plurality of coded regions.

6. The method of claim 5, wherein the plurality of coded regions are color coded.

7. The method of claim 1, wherein the determining of the safe range of radiation is based on the radiation location.

8. A method of administering radiation to a patient, the method comprising:
   receiving, at a processor associated with a radiation device, a calculated dose of radiation for a patient;
   receiving, at the processor, a radiation location for the patient;
   receiving, at the processor, at least one of: a patient characteristic and a coded region corresponding to a patient characteristic;
   correlating, at the processor, the at least one of the patient characteristic and the coded region corresponding to the patient characteristic with a safe dose range of radiation at the radiation location for the patient;
   comparing, at the processor, the calculated dose of radiation to the safe dose range; and
   applying the calculated dose of radiation to the patient at the radiation location when the calculated dose of radiation is within the safe dose range.

9. The method of claim 8, further including, when the calculated dose of radiation is not within the safe dose range:
   generating a message to display;
   displaying the message on a screen associated with the radiation device; and
   refraining from applying the calculated dose of radiation to the patient at the radiation location.

10. The method of claim 8, wherein the safe dose range for the patient varies depending on the radiation location.

11. The method of claim 8, further comprising:
   determining, at the radiation location, a second patient characteristic;
   determining, at the processor and based on the second patient characteristic, a second coded region for the patient;
   correlating, at the processor, the second coded region for the patient with a second safe dose range of radiation at the radiation location for the patient; and
   determining whether the calculated dose is within the second safe dose range.

12. The method of claim 11, wherein the calculated dose is applied when the calculated dose is within the safe dose range and the second safe dose range.

13. The method of claim 11, wherein when the calculated dose is not within the safe dose range and within the second safe dose range:
  generating a message to display; and
  displaying the message on a screen associated with the radiation device.

14. The method of claim 11, further comprising:
  determining, at the radiation location, a second patient characteristic;
  determining, at the processor and based on the second patient characteristic, a second coded region for the patient;
  generating a message to display when the second coded region is not the same as the coded region; and
  displaying the message on a screen associated with the radiation device.

15. A method of administering radiation to a patient, the method comprising:
  receiving, at a processor associated with a radiation device, a color coded region corresponding to a value of a physical characteristic of the patient wherein the color coded region is included among a plurality of color coded regions;
  receiving, at the processor, information identifying a radiation location corresponding to a location on a patient;
  determining, at the processor, that at least one of contrast media and sedation to be given to the patient;
  determining, at the processor, at least one of a dose amount and a dose concentration of the at least one of the contrast media and sedation based at least in part on the color coded region;
  determining, at the processor and based on a size of the patient, a safe range of radiation for the patient;
  correlating the color coded region and the radiation location with a dose of radiation;
  providing the at least one of the contrast media and sedation to the patient; and
  applying the dose of radiation to the radiation location.

* * * * *